United States Patent
Ishimaru et al.

[11] Patent Number: 6,127,138
[45] Date of Patent: Oct. 3, 2000

[54] METHOD OF ENZYMATICALLY MEASURING GLYCATED PROTEIN

[75] Inventors: Kaori Ishimaru; Katsutaka Ooishi; Hiroshi Fukuya; Akihiko Okamura, all of Kyoto, Japan

[73] Assignee: Kyoto Daiichi Kagaku Co., Ltd., Kyoto, Japan

[21] Appl. No.: 09/202,641

[22] PCT Filed: Apr. 24, 1998

[86] PCT No.: PCT/JP98/01904

§ 371 Date: Aug. 13, 1999

§ 102(e) Date: Aug. 13, 1999

[87] PCT Pub. No.: WO98/48043

PCT Pub. Date: Oct. 29, 1998

[30] Foreign Application Priority Data

Apr. 24, 1997 [JP] Japan .................................. 9-107106
Mar. 18, 1998 [JP] Japan ................................. 10-090836
Mar. 18, 1998 [JP] Japan ................................. 10-090837

[51] Int. Cl.[7] .............................. C12Q 1/37; C12Q 1/00; C12N 1/14

[52] U.S. Cl. .................................. 435/23; 435/24; 435/4; 435/254.7; 435/256.5; 435/256.1; 435/929

[58] Field of Search .................................. 435/23, 24, 4, 435/254.7, 256.5, 256.1, 929

[56] References Cited

U.S. PATENT DOCUMENTS 5,712,138   1/1998   Kato et al. .................................. 435/23

FOREIGN PATENT DOCUMENTS

| 0 526 150 A1 | 2/1993 | European Pat. Off. . |
| 0 576 838 A2 | 1/1994 | European Pat. Off. . |
| 2-195899 | 8/1990 | Japan . |
| 2-195900 | 8/1990 | Japan . |
| 3-155780 | 7/1991 | Japan . |
| 4-4874 | 1/1992 | Japan . |
| 5-33997 | 5/1993 | Japan . |
| 192193 | 8/1993 | Japan . |
| 48846 | 2/1994 | Japan . |
| 6-65300 | 8/1994 | Japan . |
| 7-289253 | 11/1995 | Japan . |
| 8-154672 | 6/1996 | Japan . |
| 8-336386 | 12/1996 | Japan . |

OTHER PUBLICATIONS

Luisetti M., et al.; "Some Properties of the Alkaline Proteinase from *Aspergillus Melleus*"; Int. J. Tiss. Reac. XIII(4), pp. 187–192 (1991). Month not available.

*Primary Examiner*—Louise N. Leary
*Attorney, Agent, or Firm*—Morgan, Lewis & Bockius LLP

[57] ABSTRACT

A sample containing a glycated protein is treated with Protease XIV or a protease from Aspergillus genus, thereafter (or while treating the sample with the above protease) FAOD (fructosyl amino acid oxidase) is caused to react with the sample so as to measure the amount of oxygen consumed by the FAOD reaction or the amount of the resultant reaction product, thereby to measure the glycated protein.

According to the above method, the glycated protein can be fragmented while the decomposition of the FAOD itself is prevented, thereby to facilitate the binding of the protein with the FAOD and to improve the sensitivity of the detection.

18 Claims, 8 Drawing Sheets

METHOD OF ENZYMATICALLY MEASURING GLYCATED PROTEIN

TECHNICAL FIELD

The present invention relates to a method of measuring a glycated protein by using fructosyl amino acid oxidase (hereinafter, referred to as "FAOD"). More particularly, the present invention relates to a method which is capable of measuring a glycated protein with greater accuracy and high sensitivity, and is easily applicable to clinical examination (or clinical diagnostic test), etc., and also relates to a protease which is suitably usable for such a measurement method.

BACKGROUND ART

A glycated protein is a substance which is produced by the non-enzymatic and irreversible binding of the amino group of an amino acid constituting a protein, with the aldehyde group of a reducing sugar such as aldose. Such a non-enzymatic and irreversible binding reaction is also called "Amadori rearrangement," and therefore the above-mentioned glycated protein may also be called "Amadori compound" in some cases.

The rate of the formation of the glycated protein generally depends on the concentration of the protein and the reducing sugar as raw materials for providing the above glycated protein, the time period of the contact between these raw materials, and the temperature at the time of the glycation reaction. As a matter of course, as the amount of the above protein and reducing sugar is increased, as the time period of the contact therebetween is increased, or as the temperature becomes higher (within a range such that the protein is not denatured), the rate of the formation of the glycated protein as a reaction product is increased, and the amount of the reaction product is also increased.

On the other hand, in a living organism (or "in vivo"), since the concentration of the glycated protein is changed depending on the half life of the protein as the raw material for the above glycation reaction, various kinds of information on the living organism can be obtained by measuring the concentration of the glycated protein.

Among the above-mentioned glycated proteins, for example, a fructosylamine derivative produced by the glycation of hemoglobin in blood is called "glycohemoglobin", one produced by the glycation of albumin is called "glycoalbumin", and a derivative (having a reducing ability) produced by the glycation of protein in blood is called "fructosamine".

Since the concentration of these glycated protein derivatives in blood reflects the average concentration of blood sugar in a living organism for a certain period of time in the past, the measured value of the concentration of the above glycated protein derivative in blood may be a significant indicator of the diagnosis of the symptom of diabetes and of the monitor or control of such a symptom. Accordingly, also from a clinical viewpoint, it is very useful to establish a method of measuring the concentration of the glycated protein in blood.

Heretofore, it has been known that a glycated protein in a sample (or specimen) can be measured, e.g., by causing an oxidoreductase to act on the glycated protein and measuring the amount of the oxygen consumed in this reaction or the amount of the product (such as hydrogen peroxide) based on the action of the oxidoreductase (e.g., Japanese Patent Publication (JP-B; "Kokoku") Hei-5-33997 (i.e., 33997/ 1993), JP-B Hei-6-65300, Japanese Laid-Open Patent Applications (JP-A; "Kokai") Hei-2-195900, JP-A Hei-3-155780, JP-A Hei-4-4874, JP-A Hei-5-192193, JP-A Hei-6-46846, JP-A Hei-7-289253, JP-A Hei-8-154672 and JP-A Hei-8-336386 may be referred to).

In addition, there is known a method of measuring a glycated protein for the purpose of the diagnosis of diabetes (JP-A Hei-2-195899, JP-A Hei-2-195900, JP-A Hei-5-192193 corr. to European Publication EP 0526150A, JP-A Hei-6-46846 corr. to EP 0576838A, JP-A Hei-7-289253, JP-A Hei-8-154672 and JP-A Hei-8-336386 may be referred to).

In general, an enzymatic reaction using a glycated protein as a substrate is represented by the following formula.

$$R^1\text{---CO---CH}_2\text{---NH---}R^2 + O_2 + H_2O \rightarrow R^1\text{---CO---CHO} + R^2\text{---NH}_2 + H_2O_2$$

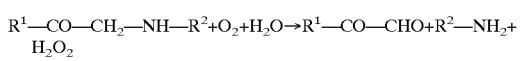

(wherein, $R^1$ represents the aldose residue of a reducing sugar and $R^2$ represents a residue of an amino acid, protein or peptide.)

As an enzyme catalyzing a reaction using the above glycated protein as a substrate, FAODs (fructosyl amino acid oxidases) from various kinds of microorganism are known. Our research group has already obtained FAODs from microorganisms belonging to Fusarium genus, Gibberella genus, Penicillium genera, etc., and has showed that these FAODs are useful for measuring a glycated protein (JP-A Hei-7-289253, JP-A Hei-8-154672 and JP-A Hei-8-336386 may be referred to).

Among the above-mentioned various kinds of FAODs, the FAOD from Fusarium oxysporum S-1F4 (hereinafter, referred to as "FAOD-S") and the FAOD from Gibberella fujikuroi (hereinafter, referred to as "FAOD-G") have an activity on fructosyl-lysine and/or fructosyl-polylysine, and therefore it has been found that these enzymes are useful for measuring human serum or human glycated albumin (JP-A Hei-7-289253).

Accordingly, it is expected that if a method of measuring a glycated protein by using these FAODs is established, the above-mentioned method using FAOD becomes applicable to a general-purpose examining apparatus, and such a measuring method can be effected with lower cost for a shorter period of time as compared with those in the conventional methods such as one using HPLC (high-performance liquid chromatography) and one using antibody. Further, in such a case, it becomes possible to accurately measure the glycated protein in a component of a living organism by utilizing the specificity of the above FAOD enzyme, and therefore the measurement of the glycated protein using the FAOD enzyme is fully expected for the mass screening examination in a medical checkup or a curative marker for diabetics.

In the measurement of a glycated protein using the FAOD, it is preferred that the glycated protein as a substrate is efficiently bound to the substrate binding site of the FAOD as an enzyme (or catalyst). Accordingly, in order to enhance the rate of the enzymatic reaction, it is important to design the substrate so as to enhance the efficiency of the above binding. The reason for this is that the FAOD has a tendency such that it has a higher activity on a glycated peptide (having a lower molecular weight than that of protein) than the activity on a glycated protein, and has a still higher activity on a glycated amino acid (having a still lower molecular weight than that of the peptide) than the activity on the glycated peptide.

With respect to the FAOD, it is well known that the reaction rate for the above-mentioned FAOD is increased by converting a glycated protein present in a living organism component into corresponding small fragments (i.e., decreasing the molecular weight of the protein) by use of a protease. As described above, it is theoretically possible to use a protease which completely digests or fragments the glycated protein into amino acids because the glycated amino acids are most preferred in view of the affinity of the substrate with the FAOD. However, such a method has a problem that it requires a considerably long period of time for the fragmentation treatment of the protein into amino acids. Accordingly, it is preferred to use a protease which selectively cleaves the glycated protein at the site of a glycated amino acid present in the protein, in view of the balance between the affinity of the FAOD with the substrate and the period of time required for the digestion or fragmentation.

However, there are many kinds of proteases, and the size or dimension of the substrate which is suitable for the FAOD enzymatic reaction may vary depending on the kind of the FAOD to be combined with the protease. Accordingly, in practice, preferred combinations of protease and the FAOD are considerably restricted.

In the above-mentioned technical field, it is known that various kinds of proteases are useful in combination with certain kinds of the FAODs, and those proteases are roughly classified into endo-type proteases and exo-type proteases.

The former, endo-type protease, is an enzyme which decomposes a protein from the internal site thereof. Specific examples thereof includes: trypsin, α-chymotrypsin, subtilisin, proteinase K, papain, cathepsin B, pepsin, thermolysin, Protease XIV, protease XVII, protease XXI, lysyl-endopeptidase, prolether, bromelain F, etc.

On the other hand, the latter, exo-type protease is an enzyme which sequentially decomposes a peptide chain from the end thereof. Specific examples thereof includes: aminopeptidase, carboxypeptidase, etc.

JP-A Hei-5-192193 discloses, as proteases useful for measuring a glycated proteins, Proteinase K, pronase E, ananine, thermolysin, subtilisin, and cow pancreas proteases. Actually, the protease disclosed in JP-A Hei-5-192193 is subjected to the fragmentation treatment of a glycated protein present in a sample, and then is inactivated by the incubation at 55° C. for 30 minutes. The reason for the inactivation of the protease is to suppress or prevent the fragmentation of FAOD per se as a catalyst by the protease, in the course of the next step of the reaction between the glycated protein and the FAOD.

If the FAOD per seas a catalyst is fragmented, as a matter of course, there is decreased the amount of oxygen to be consumed or the amount of hydrogen peroxide to be produced based on the action of the FAOD on the glycated protein, and as a result, the sensitivity for detecting the glycated protein is decreased. Further, since such fragmentation of the FAOD also has an effect on the accuracy in the results of measurement of the glycated protein per se, the above-mentioned inactivation treatment of the protease has generally been considered to be an essential treatment, as long as the protease is used in combination with the FAOD.

However, it is not easy to select a protease satisfying the above-mentioned requirement (i.e., preferable matching thereof with the FAOD) from known proteases. For example, JP-B Hei-5-33997 teaches none of specific protease, and JP-A Hei-5-192193 only discloses proteases (protease K, protease E) to be used in combination with ketoamine oxidase which has been obtained from Debliomyces genus.

Thus, according to the present inventors' experiments, it has been found that, when a glycated protein present in a sample is actually treated with the protease disclosed in the above JP-A Hei-5-192193, then the protease was inactivated by heating at 55° C. for 30 minutes, and the FAOD was reacted with the resultant product, the amount of hydrogen peroxide as a reaction product or the amount of oxygen consumed in the reaction is small, and as a result, the detection sensitivity is insufficient.

Proteases can also be inactivated by the addition of an inhibitor, other than to the heat denaturation by heating. However, there are some combinations of a protease and an inhibitor which cannot completely inactivate the protease (i.e., wherein a certain degree of protease activity still remains).

The above inactivation of the protease is based on the phenomenon that the inhibitor binds to the active center of the protease to which the substrate is to be bound. In order to cause the inhibitor to bind to the active center of the protease, it is necessary to add the inhibitor to the reaction system after the completion of the protease reaction, and then to cause a reaction to occur at a certain temperature for a certain period of time after the addition of the inhibitor. Accordingly, the period of time required for the entire measurement of the glycated protein is increased by the period of time required for the inactivating reaction of the protease.

An object of the present invention is to provide a method of enzymatically measuring a glycated protein which can solve the problems encountered in the prior art, and to provide an enzyme which is preferably applicable to such a measurement method.

Another object of the present invention is to provide a method of measuring a glycated protein with better accuracy and higher sensitivity, and to provide an enzyme which is preferably applicable to such a measurement method.

DISCLOSURE OF INVENTION

As a result of earnest study, the present inventors have found that a specific protease provides good matching with an FAOD which is suitable for measuring a glycated protein (such as glycated albumin) in a living organism component in various aspects, whereby the glycated protein can be measured with accuracy and high sensitivity, and that such a combination is very useful for achieving the above-mentioned object.

The protease according to the present invention is based on the above discovery, and is a protease to be used for measuring a glycated protein in a sample in combination with FAOD (fructosyl amino acid oxidase).

The present invention also provides a method of measuring a glycated protein by causing FAOD to act on a sample containing a glycated protein, wherein the glycated protein is treated with a protease under an acid condition.

The present invention further provides a method of measuring a glycated protein by causing protease and FAOD to act on a sample containing a glycated protein, wherein a protease from Aspergillus genus is used as the protease.

The present invention further provides a method of measuring a glycated protein by causing protease and FAOD to act on a sample containing a glycated protein, wherein Protease XIV is used as the protease.

BEST MODE FOR CARRYING OUT THE INVENTION

Figure 1:
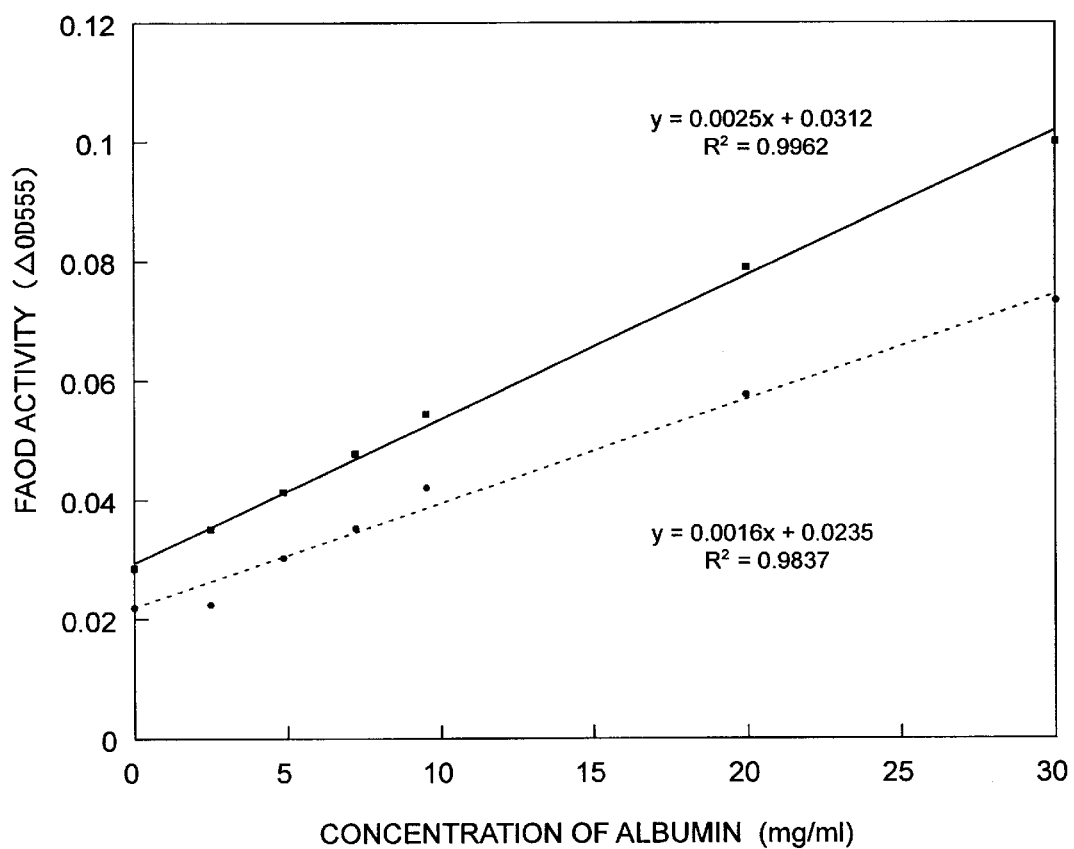
FIG. 1 is a graph showing a relationship between the concentration of glycated albumin and the resultant absorbance (glycated albumin measurement-albumin reagent) in Example appearing hereinafter.

Hereinbelow, the present invention will be described in detail, with reference to the accompanying drawings as desired.

(Sample)

In the measurement method according to the present invention, it is possible to use any sample (or specimen) containing a glycated protein (typically, a sample produced by or taken out from a living organism). Specific examples of the sample may include those from a living organism such as blood (whole blood, plasma or blood serum) and urine.

In general, the treatment of the above-mentioned sample with a protease may be conducted in accordance with an instruction manual available from the corresponding supplier. For example, it is preferred to incubate the sample with the protease in a Tris-HCl buffer (pH 8.0) for about 30 minutes at 50° C. in the case of the Sumizyme MP (trade name; mfd. by Sin Nippon Kagaku Kogyou Co. Ltd.) appearing hereinafter, or at 37° C. in the case of the Protease XIV (trade name; mfd. by Sigma Co.), as the above-mentioned protease.

(Protease)

In the present invention, in view of provision of good detection sensitivity, it is preferred to select the protease to digest or fragment a glycated protein in a sample, in accordance with an FAOD to be used in combination therewith.

As the above-mentioned protease, it is possible to use one kind of protease, or plural kinds of proteases in a combination or in a mixture thereof. At this time, as desired, it is also possible to use plural kinds of proteases so as to fragment a glycated protein more specifically and to enhance the sensitivity of the detection.

In the present invention, Protease XIV (trade name; mfd. by Sigma Co.) or a protease from Aspergillus genus may preferably be used, in view of easiness in the accurate measurement of the glycated protein. As the protease from Aspergillus genus, a protease from *Aspergillus melleus* (hereinafter, referred to as "*A. melleus*") may particularly preferably be used.

Preferred examples of such a protease from *A. melleus* may include: a protease from a specific *A. melleus* strain (name and address of the depositary institution: National Institute of Bioscience and Human-Technology, Agency of Industrial Science and Technology, Ministry of International Trade and Industry; 1–3, Higashi 1-Chome, Tsukuba-shi, Ibaraki-ken, 305-8566 JAPAN; date of deposition: Mar. 3, 1998; deposition number: FERM BP-6277). It has been confirmed by the present inventors' investigation that this protease has substantially the same enzymatic characteristics as those of the commercially available protease "Sumizyme MP" to be described below (the same degree of matching property with the FAOD, or the same degree of activity; as described in Example 4 appearing hereinafter).

The above-mentioned protease from *A. melleus* includes those having an optimum pH value in the basic range and those having an optimum pH value in the acidic range. Both of these types of proteases are usable in the present invention.

Similarly, specific examples of the *A. melleus*-produced protease to be preferably usable in the present invention may include: Sumizyme MP (trade name; mfd. by; SHIN NIHON CHEMICAL CO., JP) which is used in the field of food processing. Sumizyme MP is used as an enzyme for use in the food industry, and it is inexpensive and can be supplied in a large quantity. Accordingly, this enzyme is advantageously usable in view of the application thereof to clinical examination such as screening.

Generally, the site of a glycated protein at which glycation occurs is determined by the kind of the protein, more specifically, by the kind and position (or site) of amino acids constituting the protein. When the above-mentioned protein is albumin, the position thereof which is most liable to be glycated is the lysine at a 525th position counted from the N-terminal of the albumin, and in most of glycated albumin, the lysine at the 525th position counted from the N-terminal is glycated. Accordingly, if a protease which preferably fragments this glycated lysine is used, the sensitivity of the detection would be improved. The above-mentioned "Protease XIV" or protease from Aspergillus genus such as *A. melleus* (e.g., Sumizyme MP) may preferably be used also from such a viewpoint.

Further, in the present invention, it is preferred to use a protease which can easily be inactivated by using a simple treatment after the use thereof in the protease treatment. Specific examples of the simple treatment may include a pH change, heating, addition of an inhibitor, etc. (Protease having optimum pH in acidic range)

In the present invention, a protease having an optimum pH value in the acidic range (i.e., pH value less than 7.0) may also be used, as long as it has a characteristic such that it can effectively fragment or cleavage the glycated amino acid at the glycated site of the glycated protein, can increase the absolute amount of oxygen consumed in the reaction based on FAOD, or the absolute amount of the reaction product (e.g., hydrogen peroxide) produced thereby, and can enhance the sensitivity of the detection.

When such a protease having an optimum pH value in the acidic range is used, it is possible to inactivate the protease after the fragmentation of the glycated protein, by simply adjusting the pH value to the optimum pH value of the FAOD (in the basic pH range, e.g., pH=8). Accordingly, in such a case, after the inactivation of the protease, the operation for the FAOD reaction can be extremely simplified, and the treatment can be conducted rapidly. In the method of adjusting the pH value, any operation for inactivating the protease by heating denaturation or addition of an inhibitor can be omitted.

Specific examples of such a protease having an optimum pH value in the acidic range may include a protease having its an optimum pH value in the acidic range which can be isolated or purified from the proteases from the above-mentioned A. melleus.

(Inactivation of protease)

In the measurement of the glycated protein according to the present invention, for example, it is possible to initiate the FAOD reaction after the fragmentation treatment of the glycated protein, by inactivating the protease and adding the FAOD. It is preferred to suppress or prevent the above-mentioned fragmentation treatment of the FAOD with the protease, by utilizing such protease inactivation.

(FAOD)

In the present invention, it is preferred to select an optimum FAOD in accordance with the kind of the glycated protein as an analyte or target for the measurement, since the glycation site is determined by the relationship with a living organism component (e.g., kind and position of amino acids constituting the protein).

Specific examples of the FAOD usable in the present invention may include: those which can be induced by cultivating microorganism or bacteria belonging to Fusarium genus, Gibberella genus, Penicillium genus, Aspergillus genus, etc. in the presence of fructosyl lysine and/or fructosyl $N^\alpha$-Z-lysine. Such FAOD can be obtained, e.g., by the method as disclosed in JP-A Hei-7-289253, JP-A Hei-8-154672, JP-A Hei-8-336386, etc.

In the present invention, among the above FAODs, it is particularly preferred to use the FAOD-S from Fusarium oxysporum S-1F4 described above or the FAOD-G from Gibberella fujikuroi AKU 3802 (JP-A Hei-7-289253) in view the activity thereof on fructosyl lysine and/or fructosyl polylysine, as the sites in human serum or human glycated albumin which are easily glycated.

(Titer of FAOD)

The titer of the FAOD to be used in the present invention may preferably be measured by the following method.

(1) Method of Measuring Hydrogen Peroxide as Reaction Product by Use of Colorimetry A. Rate Method 100 μl of 100 mM fructosyl $N^\alpha$-Z-lysine (FZL)-45 mM 4-aminoantipyrine-60 units/ml peroxidase solution and 100 μl of 60 mM phenol solution are mixed with 1 ml of 0.1 M Tris-HCl buffer (pH value 8.0) and 50 μl of an enzyme solution (of FAOD the titer of which is to be measured), and then distilled water is added to the resultant mixture so as to provide a total volume of the mixture of 3.0 ml.

The resultant solution is incubated at 30° C. for 2 minutes, and then 50 μl of 100 mM of fructosyl $N^\alpha$-Z-lysine (FZL) solution is added thereto, and the resultant mixture is subjected to the measurement of the absorbance thereof at 505 nm with the elapse of time. The amount (micro-moles) of hydrogen peroxide produced per one minute is calculated by use of the molar absorption coefficient of the quinone dye ($5.16\times10^3$ $M^{-1}cm^{-1}$) formed by this reaction, and the resultant value is regarded as an enzyme activity unit (U).

B. End-point Method

In the same manner as in the above "method A", the substrate (FZL) is added and the incubation is conducted at 30° C. for 30 minutes, and thereafter the resultant mixture is subjected to the measurement of the absorbance thereof at 505 nm. Then, the enzyme activity is calculated by use of a calibration curve which has preliminarily been prepared.

(2) Method of Measuring Oxygen Absorption by Enzymatic Reaction 1 ml of 0.1 M Tris-HCl buffer (pH value 8.0) and 50 μl of an enzyme solution are mixed, and the total volume of the mixture is adjusted to 3.0 ml by use of distilled water. The resultant mixture is transferred into an oxygen electrode cell mfd. by Rank-Brothers Co.

The above-mentioned solution in the cell is stirred at 30° C. so that the temperature thereof and the oxygen dissolved therein assume an equilibrium state, and thereafter 100 μl of 50 mM FZL is added to the resultant solution and the absorption of oxygen is continuously measured by use of a recorder so as to determine the initial rate thereof. By use of a standard curve, the amount of oxygen absorbed per one minute is calculated and the resultant value is regarded as an enzyme unit.

(Method of measuring glycated protein)

In the method of measuring a glycated protein according to the present invention, it is preferred that, while a glycated protein in a sample is treated with the above-mentioned protease so as to provide a state of the glycated protein with which the FAOD is liable to react, or after the glycated protein is treated with a protease, the FAOD is reacted with the resultant product so as to measure the amount of oxygen consumed in the above FAOD-substrate reaction or the amount of the reaction product produced by the reaction.

The reaction of the glycated protein (or product produced by the treatment thereof with protease) with the FAOD produces hydrogen peroxide and glucosone. Both of the hydrogen peroxide and glucosone can be used as the FAOD reaction product which is an analyte to be measured in the subsequent step. The method of measuring the FAOD reaction product is not particularly limited, but may be one which is appropriately selected from known methods.

The amount of the hydrogen peroxide can be quantitatively determined by use of any method known in the above-mentioned technical field, such as colorimetry method or color-developing method (e.g., a measurement method employing a chromogen which is capable of producing a dye or coloring matter along with the decomposition thereof by a catalyst having a peroxidase or peroxidase-like activity), a measurement method using an electrochemical technique (e.g., a method using a hydrogen peroxide electrode), a method of measuring the amount of aldehyde produced from hydrogen peroxide in the presence of catalase and an alcohol.

In the present invention, e.g., it is possible to quantitatively determine the glycated protein by use of a calibration curve which has preliminarily been provided by using the above-mentioned measurement method and samples respectively containing known amounts of the glycated protein. At this time, it is preferred that the activity of the FAOD is constant. As desired, a sample containing a living organism component, etc., may preferably be subjected to the measurement after the sample is diluted with a buffer solution.

(Color-developing system)

As the color-developing system for the colorimetry method using hydrogen peroxide, it is possible to use a system which produces a coloring matter through oxidation condensation between a coupler such as 4-amino antipyrine (4AA) and 3-methyl-2-benzothiazolynon hydrazone (MBTH), and a chromogen such as phenol in the presence of peroxidase.

Examples of the chromogen can include phenol derivatives, aniline derivatives, toluidine derivatives, etc. Specific examples of the chromogen may include N-ethyl-N-(2-hydroxy-3-sulfopropyl)-m-toluidine, N,N- dimethylaniline, N,N-diethylaniline, 2,4-dichlorophenol, N-ethyl-N-(2-hydroxy-3-sulfopropyl)-3,5-dimethoxyaniline, N-ethyl-N-(3-sulfopropyl)-3,5-dimethylaniline (MAPS), N-ethyl-N-(2-hydroxy-3-sulfopropyl)-3,5-dimethylaniline (MAOS), etc.

Further, it is also possible to use as the above-mentioned chromogen, a known leuco-type color-developing reagent which develops a color through the oxidation thereof in the presence of peroxidase. Specific examples of the color-developing reagent may include o-dianisidine, o-tolidine, 3,3-diaminobenzidine, 3,3,5,5-tetramethylbenzidine, N-(carboxymethylaminocarbonyl)-4,4-bis(dimethylamino) biphenylamine (DA 64), 10-(carboxymethylaminocarbonyl)-3,7-bis(dimethylamino) phenothiazine (DA 67), etc.

(Other measurement methods)

In addition to the above-mentioned colorimetry method, a method utilizing fluorescence or chemiluminescence can also be used so as to measure the hydrogen peroxide by using the chromogen.

In the fluorescence method (or fluolometry), it is possible to use a compound which is capable of giving fluorescence through the oxidation thereof, such as homo-vanillic acid, 4-hydroxyphenyl acetic acid, tyramine, para-cresol, and diacethyl fluorescin derivative. In the chemiluminescence method, it is possible to use peroxidase, potassium ferricyanide, hemin, etc., as a catalyst, and to use luminol, lucigenin, isoluminol, pyrogallol, etc., as a substrate.

Further, in the above-mentioned measurement of hydrogen peroxide, it is also possible to use a system in which catalase is reacted therewith in the presence of an alcohol (such as methanol) and the resultant aldehyde is treated by haunch reaction or the above-mentioned condensation reaction using MBTH so as to develop a color. It is possible that the thus produced aldehyde is conjugated with aldehyde dehydrogenase and the resultant change in NAD (NADH) is measured.

On the other hand, a known aldose reagent, such as diphenylamine, can be used so as to measure the glucosone which is an FAOD reaction product other than hydrogen peroxide.

(Measurement using electrode)

When the hydrogen peroxide as an FAOD reaction product is measured by use of an electrode, the material of the electrode is not particularly limited as long as the material can transfer (donate or withdraw) electrons with respect to the hydrogen peroxide. Preferred examples of such a material may include platinum, gold, silver, etc. The measurement using an electrode can be effected by a known method in the art, such as amperometry, potentiometry and coulometry.

Further, it is also possible to measure the glycated protein by causing an electron-transporting carrier to be concerned in the reaction as an intermediary between the electrode and FAOD or substrate, and measuring the amount of oxidation-reduction electric current or quantity of electricity. The above-mentioned electron-transporting carrier may be any known material which is capable of transporting electrons, and specific examples thereof may include ferrocene derivatives, quinone derivatives, etc.

Further, it is also possible to measure the glycated protein by causing an electron-transporting carrier to be concerned in the reaction as an intermediary between the electrode and the hydrogen peroxide produced by the FAOD reaction, and measuring the amount of oxidation-reduction electric current or quantity of electricity.

EXAMPLES

Hereinbelow, the present invention will be described in more detail with reference to Examples.

Example 1

(Primary screening of proteases)

As the primary screening of proteases, a glycated protein was fragmented by use of each of these proteases, and thereafter the resultant product was reacted with FAOD-G as an FAOD, and the amount of the resultant hydrogen peroxide was measured.

(1) Materials

Enzyme to be examined: proteases described in Table 1 appearing hereinafter

Substrate: Human serum albumin (trade name: Alb, mfd. by SIGMA Co.)

Human serum (serum, Bio Whittaker)

FAOD: FAOD-G (FAOD-G was isolated and purified from Gibberella fujikuroi by use of the method described in JP-A Hei-7-289253)

Chromogen: 4-amino antipyrine

N-ethyl-N-(2-hydroxy- 3-sulfopropyl)-m-toluidine

Buffer: 0.1M Tris-HCl buffer (pH value 8.0)

(2) Protease Treatment

500 µl of human serum albumin or human serum, which had been prepared by using the above 0.1M Tris-HCl buffer (pH value 8.0) so as to provide a concentration thereof of 5% was mixed with 500 µl of each of proteases which had been prepared by use of a buffer having an optimum pH value for each protease so as to provide a value of 10 U/ml, and the resultant mixture was incubated for 30 minutes at the optimum temperature for each enzyme, and then was heated at about 90° C. for 5 minutes to stop the protease reaction.

(3) FAOD Reaction

An "FAOD reaction mixture" having the following composition was prepared.

Supernatant of protease-treated solution obtained in the above treatment (2) 400 µl FAOD-G (3 U/ml) 10 µl 3 mM 4-amino antipyrine solution 30 µl 3 mM N-ethyl-N-(2-hydroxy-3-sulfopropyl)-m-toluidine solution 30 µl peroxidase solution (60 U/ml) 30 µl 0.1 M Tris-HCl buffer (pH value 8.0) 500 µl The FAOD reaction mixture having the above composition was incubated at 37° C. for 30 minutes and the absorbance thereof was measured at 555 nm. A blank for each sample, i.e. the absorbance based on a reference solution containing no FAOD, was also measured, and the absorbance of the blank was subtracted from the absorbance of each sample obtained by the above step thereby to obtain the actual absorbance data.

According to the above-mentioned steps, the amount of hydrogen peroxide produced by the reaction of the each protease-treated product and the FAOD was determined by use of the absorbance thereof, and in order to evaluate the usefulness of each protease, each measured value was converted into relative activity as compared with the standard value (100%) which was the absorbance obtained by the Protease XIV treatment.

The results obtained by the above-mentioned measurements are inclusively shown in the following Tables 1 and Table 2.

TABLE 1

Middle-temperature range proteases

| Temperature | Protease | relative activity (%) Alb | Serum |
|---|---|---|---|
| 25° C. | 1. Aminopeptidase | 10 | 34 |
| | 2. Aminopeptidase I | 6 | 21 |
| | 3. Carboxypeptidase B | | 59 |
| | 4. Carboxypeptidase Y | 2 | 115 |
| | 5. Cathepsin B (bovine) | | 44 |
| | 6. Leucine aminopeptidase (cytosol) | 56 | 42 |
| | 7. Papain | | 21 |
| | 8. Protease A | 9 | 6 |
| | 9. Trypsin | | 5 |
| | 10. TPCK Trypsin | | 5 |
| | 11. Chymotrypsin | | 6 |
| 30° C. | 12. Lysylendopeptidase | 4 | 11 |
| | 13. Subtilisin A | 13 | 47 |
| | 14. Protease (type XXI) | 9 | 7 |
| 37° C. | 15. Achromopeptidase | | 21 |
| | 16. Lysine aminopeptidase | 8 | 25 |
| | 17. Pronase E | 99 | 58 |
| | 18. Protease | 86 | 39 |
| | 19. Protease (type XIV) | 100 | 100 |
| | 20. Protease (type XVII) | | 24 |
| | 21. Protenase | 5 | 91 |

TABLE 2

High-temperature range protease

| Temperature | Protease | relative activity (%) Alb | Serum |
|---|---|---|---|
| | Protease (type XIV) | 100 | 100 |
| 50° C. | 22. Human liver cathepsin B | | |
| | 23. Pronase | 65 | 86 |
| | 24. Protease A | 90 | |
| | 25. Protease M | 12 | |
| | 26. Protease N | 22 | 50 |
| | 27. Protease P | 51 | 74 |
| | 28. Papain W-40 | 11 | 34 |
| | 29. Sumizyme LP50 | 17 | 32 |
| | 30. Sumizyme LPL | | 26 |
| | 31. Sumizyme MP | 150 | 136 |
| | 32. Sumizyme FP | | 18 |
| | 33. Protin PC10 | 25 | |
| 60° C. | 34. Penicilloprotenase | | |
| | 35. Protease S | 138 | 74 |
| | 36. Protin A | 37 | 91 |
| | 37. Protin FA | 39 | 185 |
| | 38. Thermoase | 99 | 20 |
| | 39. Bromelain F | 35 | 69 |
| | 40. Proleser G | 32 | 44 |
| | 41. Sumizyme AP | 39 | 122 |

Based on these results of the primary screening (Tables 1 and 2), ten kinds of proteases were selected since they mainly provided high absorbance for both human serum albumin (HSA) and human serum substrates.

Example 2
(Secondary screening of proteases)

In this Example, with regard to the above-mentioned FAOD-S and FAOD-G as the FAOD, the ten kinds of proteases selected in Example 1 were subjected to a secondary screening. The FAOD-S used herein was isolated and purified by the method described in JP-A Hei-7-289253.

In the secondary screening, measurement was performed in the same manner as in Example 1, except that the amount of the FAOD-S used in one measurement was changed to 0.06 U (6 U/ml, 10 $\mu$l).

The results obtained in the secondary screening are shown in the following Table 3.

TABLE 3

| | Alb | | Serum | |
|---|---|---|---|---|
| | FAOD activity ($\Delta$OD 555) | | | |
| Protease | S | G | S | G |
| Protease XIV | 0.1350 | 0.1100 | 0.0570 | 0.0428 |
| Leucine aminopeptidase | 0.0037 | 0.0025 | 0.0011 | 0.0191 |
| Trypsin | 0.0064 | 0.0143 | 0.0065 | 0.0008 |
| Protease | 0.0962 | 0.0756 | 0.0481 | 0.0318 |
| Protease | 0.1273 | 0.0940 | 0.0520 | 0.0274 |
| Protenase K | 0.0496 | 0.0501 | 0.0217 | 0.0216 |
| Protease S | 0.0681 | 0.0210 | 0.0161 | 0.0135 |
| Sumizyme AP | 0.0110 | ND | ND | ND |
| Sumizyme MP | 0.1477 | 0.1205 | 0.0553 | 0.0464 |
| Protin FA | 0.0170 | ND | 0.0284 | 0.0725 |

As shown in the above Table 3, it was found that both of the FAOD-S and the FAOD-G had a similar tendency with respect to each of the proteases. Accordingly, as the most preferred protease too be used for measuring the glycated albumin in combination with the FAOD, there were selected Sumizyme MP and Protease XIV which provided high measurement values with respect to both of the human serum albumin (HSA) and human serum substrates.

Example 3
(Measurement of glycated albumin using Sumizyme MP and FAOD-G or FAOD-S)

Human serum albumin was diluted with a buffer so as to provide concentrations of 0, 5, 10, 15, 20, 25 and 30 mg/ml, thereby to prepare samples to be measured. Then, in the same manner as in Example 2, the samples were digested or fragmented by use of Sumizyme MP, then the FAOD-S or FAOD-G was reacted with the resultant product, and the amount of hydrogen peroxide produced in this reaction was measured in terms of the absorbance thereof. The thus obtained results are shown in FIG. 1.

In FIG. 1, the ordinate shows the absorbance at 555 nm, and the abscissa shows the concentration of albumin. From the results shown in FIG. 1, it was confirmed that when Sumizyme MP was used as the protease, the color development based on the action of the FAOD on the above-mentioned sample showed a good proportional relationship with respect to the concentration of the glycated albumin, and therefore Sumizyme MP was a useful protease for measuring the glycated human albumin.

Example 4
(Various investigations on protease from A. melleus having optimum pH value in basic range)

Investigations were conducted with respect to the following five strains of A. melleus, i.e., A. melleus strain (deposition number: FERM BP-6277) and strains obtained from IFO (Institute for Fermentation Osaka).

A. melleus (deposition number: FERM BP-6277)

A. melleus IFO 4339

A. melleus IFO 4420

A. melleus IFO 7541

A. melleus IFO 32035

(Renaturation and culture of strains)

The above-mentioned five strains were those which had been stored in a freeze-dried condition in ampoules, respectively, and therefore they were renatured by using 200 μl of a designated renaturation solution having the following composition, and then were inoculated into a GPYM slant having the following composition. Each of them was cultured at 30° C. for 2 days, and then it was found that all the strains were grown. The resultant slants were stored at 4° C. In the case of culturing thereof, each of the strains was subcultured into the corresponding culture medium by use of the thus obtained slants.

| <Composition of renaturation solution> | |
|---|---|
| Polypepton | 0.5% |
| Yeast extract | 0.3% |
| $MgSO_4 \cdot 7H_2O$ | 0.1% |

(The mixture having the above composition was adjusted to a pH value of 7 and then was subjected to autoclave treatment (120° C., for 20 minutes)).

| <Composition of GPYM slant> | |
|---|---|
| Glucose | 1.0% |
| Pepton | 0.5% |
| Yeast extract | 0.3% |
| Malt extract | 0.3% |
| Agar | 2.0% |

(The above-mentioned components other than agar were dissolved in distilled water, and the pH value of the resultant mixture was adjusted to 5.5–6 and the mixture was measured by using a measuring cylinder (weighed), and then agar was added to the resultant mixture and was dissolved therein by use of a microwave oven. The resultant composition was divided into test tubes so as to provide an amount thereof of 8 ml in each test tube, and then was subjected to autoclave treatment (120° C., for 20 minutes). Then, the mixture was hardened while the tube was in a slanted state.)

Thereafter, each strain was inoculated into 10 ml of a GPYM medium having the following composition, and then was cultured by a shaking culture method at 30° C. for 2 days. Then, the resultant product was transferred into 500 ml of the same medium and was further cultured for 2 days. The rate of shaking was 111 rpm for both culture steps.

| <composition to GPYM medium> | |
|---|---|
| Glucose | 1.0% |
| Pepton | 0.5% |
| Yeast extract | 0.3% |
| Malt extract | 0.3% |

(The above-mentioned components were dissolved in distilled water, and the pH value of the resultant mixture was adjusted to 5.5–6, and was then subjected to autoclave treatment (120° C., for 20 minutes)).

As a result of the above culturing, each of the strains showed good growth. Then, bacterial cells were collected or harvested by filtration, and the cells were weighed (wet weight). The thus obtained results are shown below.

| <Cell weight (wet weight) of A. melleus> | |
|---|---|
| A. melleus FERM BP-6277 | 20.6 g |
| A. melleus IFO 4339 | 20.7 g |
| A. melleus IFO 4420 | 11.1 g |
| A. melleus IFO 7541 | 8.5 g |
| A. melleus IFO 32035 | 16.3 g |

The Sumizyme MP-like protease was assumed to be an extracellular enzyme, and therefore the culture supernatant obtained above was used for the subsequent investigation. The collected cells were stored at −20° C.

(Partial purification of culture supernatant)

100 ml of the culture supernatant after the collection of the cells obtained by the above-mentioned step was concentrated and partially purified by precipitation using ammonium sulfate. Since Sumizyme MP to be selected by screening was stable in the vicinity of neutral pH value and the pH value of the cultured medium at the end of culture was approximately 4.6–5, the pH value was maintained at 6–6.5 during the precipitation using ammonium sulfate. The ammonium sulfate was added under cooling in an ice bath, and the resultant mixture was stirred at 4° C. for 1 hour after the addition of ammonium sulfate. After the stirring, the resultant mixture was centrifuged at 10000 rpm at 4° C. for 40 minutes so as to collect the resultant precipitate, and the precipitate was dissolved in a minimum amount of distilled water and was subjected to dialysis at 4° C. over night. Distilled water was used as the external solution for dialysis.

After the dialysis, the resultant internal fluid was centrifuged in a micro-tube (4° C., 12,000 rpm, 20 minutes). After the centrifugation, the resultant supernatant was collected and the volume thereof was measured. The thus obtained results are shown below.

| <pH value of culture supernatant and pH value of mixture at the time of completion of addition of ammonium sulfate> | |
|---|---|
| A. melleus FERM BP-6277 | pH 4.8 → pH 6.264 |
| A. melleus IFO 4339 | pH 5 → pH 6.4 |
| A. melleus IFO 4420 | pH 5.068 → pH 6.008 |
| A. melleus IFO 7541 | pH 4.650 → pH 6.030 |
| A. melleus IFO 32035 | pH 4.967 → pH 6.000 |

| <Volume of concentrated culture supernatant after dialysis> | |
|---|---|
| A. melleus FERM BP-6277 | 1.6 ml |
| A. melleus IFO 4339 | 3 ml |
| A. melleus IFO 4420 | 2 ml |
| A. melleus IFO 7541 | 3.8 ml |
| A. melleus IFO 32035 | 2.2 ml |

As shown by the above results, it was found that the volume of the concentrated culture supernatant after the dialysis was 1.6–3.8 ml. As compared with the volume (100 ml) thereof before the addition of the ammonium sulfate, the ratio of concentration was several tens times.

(Measurement of protease activity)

The protease activity of each of the concentrated culture supernatants (five kinds of proteases) obtained by the above-mentioned step was measured. At the time of the measurement of the protease activity, 20 μl of the above concentrated culture supernatant, 20 μl of 5 wt. % of HSA (pH 8) as a substrate, and 60 μl of 0.1 M Tris-HCl buffer (pH 8.0) were mixed and the resultant mixture was then subjected to reaction at 37° C. for 30 minutes. Then, 100 μl of 0.6 M trichloroacetic acid (TCA) was added, and the resultant mixture was left standing for 15 minutes or more under cooling in an ice bath and thereafter was subjected to centrifugation at 4° C. at 12000 rpm for 10 minutes so as to isolate protein (TCA precipitation).

To 25 μl of the supernatant obtained by the above-mentioned TCA precipitation, there were added 125 μl of Reagent-A and 1000 μl of Reagent-B of Bio-Rad DC Protein assay kit (mfd. by Bio-Rad Co.), and left standing for 15 minutes at room temperature. Then, the absorbance of the resultant product was measured at 750 nm so as to measure free amino acid in the above supernatant. In order to avoid counting the amino acid which had originally been present in the culture medium as the protease activity at the time of the above measurement of the free amino acid, a sample which had been subjected to the protease reaction for 0 min, was treated in the same manner as in the treatment of other samples, and the resultant sample was used as a blank reference.

As a result of the above measurement, all the five kinds of the concentrated cell supernatants showed clear color development after the reaction for 30 minutes, and the presence of protease activity was confirmed therein.

Further, the thus obtained results were compared with the amount of free amino acid cleaved by Sumizyme MP which had been prepared so as to provide an activity of 1 mg/ml (260 U/ml), whereby the activity of each protease with respect to HSA was roughly calculated. The thus obtained results are shown below.

| <Protease activity (as compared with Sumizyme MP, 1 mg/ml, 260 U/ml) | | |
|---|---|---|
| A. melleus FERM BP-6277 | 0.2087 mg/ml | 54.5 U/ml |
| A. melleus IFO 4339 | 0.1252 mg/ml | 32.5 U/ml |
| A. melleus IFO 4420 | 0.5144 mg/ml | 113.5 U/ml |
| A. melleus IFO 7541 | 0.0953 mg/ml | 25.0 U/ml |
| A. melleus IFO 32035 | 0.3298 mg/ml | 85.5 U/ml |

(Determination of optimum pH of protease)

The optimum pH value of a protease was measured by changing the pH value of the buffer constituting the reactant solution for measuring the activity to be used in the above "protease activity measurement."

With respect to the pH range which could not boon covered with the 0.1 M Tris-HCl buffer, 0.1 M potassium phosphate buffer and 0.1 M glycine—NaOH buffer were used. The temperature for the reaction was set to 37° C. The protease activity was measured at a pH range from 4 to 13. The pH value used herein were set at intervals of 0.5 with respect to the pH range of 7–10, and the pH values were set at intervals of 1.0 with respect to the other pH range.

Figure 2:
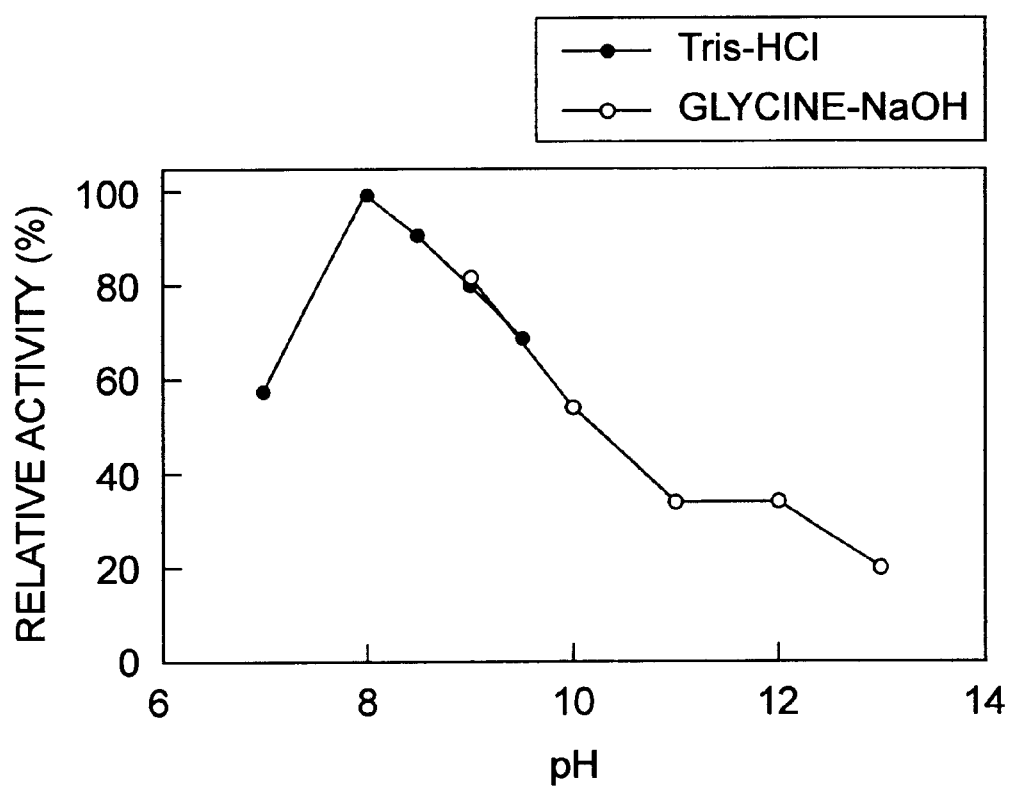
FIG. 2 is a graph showing the pH-dependency of the relative activity of a protease (optimum pH of *A. melleus* BP-6277 protease) in Example.

As a result, it was confirmed that each of the five kinds of enzymes had its optimum pH value within a pH range of 8–9 which was substantially the same as that of Sumizyme MP. The pH dependency of the protease from A. melleus FERM BP-6277 is shown in the graph of FIG. 2. In this graph, the enzyme activity is shown in terms of relative activity based on the activity in the above-mentioned optimum pH value as a standard (activity in the optimum pH value is treated as "100").

Further, a peak of the activity was also observed in the acidic range. The activity of the "acid protease" was equal to or more than that of a weak-alkali protease. If these proteases were extracellular enzymes, and a protease having the highest activity at the pH value of the culture medium was secreted in a large amount, this situation was expected to occur with high possibility, since the pH value of the medium was largely shifted to the acidic range at the end of the culturing.

Various characteristics of the acid proteases from A. melleus were also confirmed in Examples appearing hereinafter.

(Determination of optimum temperature of protease)

The optimum temperature was measured at a fixed pH value of the buffer of 8.5 while the temperature was changed from 15 to 70° C. at intervals of 5° C. The activity thereof was measured in the same manner as in the protease activity measurement after it was subjected to a digestion reaction for 30 minutes.

Figure 3:
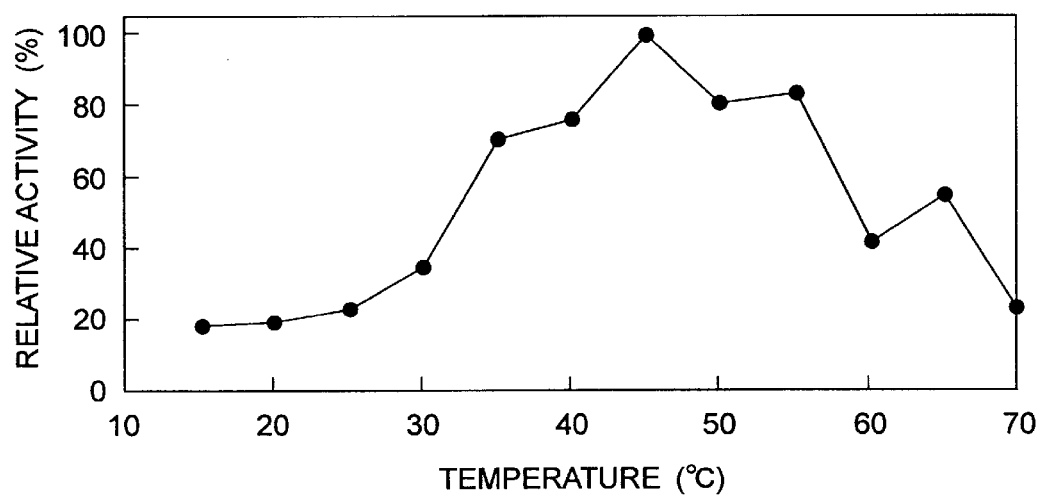
FIG. 3 is a graph showing the temperature dependency of the relative activity of a protease (temperature dependency of *A. melleus* BP-6277 protease) in Example.

As a result of the above measurement, it was found that each of the five kinds of enzymes had an optimum temperature at 45° C. or 50° C. The temperature dependency of the protease from A. melleus FERM BP-6277 is shown in the graph of FIG. 3. In this graph, the enzyme activity is shown in terms of relative activity value based on the activity in the optimum temperature as a standard (activity in the optimum temperature is treated as "100"). The above-mentioned characteristic is very similar to that of "Sumizyme MP" (which practically shows its action in the range of 45–50° C. and has its optimum temperature at 50° C.).

(Estimation of molecular weight of protease from A. melleus FERM BP-6277)

Then, the protease from A. melleus FERM BP-6277, the activity of which on a synthetic peptide was similar to that of "Sumizyem MP" was subjected to GPC (gel filtration chromatography). Superdex 200 pg 16/60 was used as a column and each of the resultant fractions was collected at intervals of 30 seconds. By measuring the protease activity of each fraction, the molecular weight of the protease was estimated by use of the time corresponding to the elution of the fraction.

| <Conditions of GPC> | |
|---|---|
| Column: | Supordex 200 pg 16/60 (Pharmacia Co.) |
| Eluent: | 20 mM Tris-HCl buffer |
| Flow rate: | 0.5 ml/min |
| Temperature: | Room temperature |
| Detector: | UV (220 nm) |
| Injected volume: | 50 μl |

In the measurement of the protease activity, in consideration of the dilution ratio, etc., of the protease during the GPC process, 80 μl of each fraction was added to 20 μl of 0.5 wt. % HSA, and subjected to reaction at 37° C. overnight. The procedure after the addition of TCA was effected in accordance with the above-mentioned "protease activity measurement."

As a result, among the respective fractions obtained by the GPC, the fraction Nos. 41–43 showed a high activity, and therefore the molecular weight of the protease from this strain was presumed to be 18382–22130.

(Measurement of glycation ratio for HSA using Sumizyme MP)

Then, the measurement of glycation ratio for HSA was tried. First of all, the glycation ratio was measured by using Sumizyme MP. Each of HSAs (SIGMA Co., Albumin Human Fraction V) having the glycation ratios of 11.7, 22.5 and 26.0% (the glycation ratio was measured by use of KDK GAA-2000 (HPLC method) mfd. by Kyoto Daiichi Kagaku Co., Ltd.) was dissolved so as to provide a concentration of 5% (pH value 8). The HSA having a glycation ratio of 11.7% was mixed with an equal volume of each of the other two kinds of HSAs so as to prepare HSAs having the glycation ratios of 17.1% and 18.85% for convenience.

To 200 μl of 5 wt. % of HSA, 100 μl of 0.1 M Tris-HCl buffer and 100 μl of Sumizyme MP (10 mg/ml) were added, and then the resultant mixture was subjected to protease reaction at 37° C. for 4 hours. Thereafter, by use of the FAOD-S (0.5602 U/ml), the activity thereof was confirmed by use of the following 4AA-TOOS color-developing system.

| <Composition of FAOD reaction mixture> | |
|---|---|
| Solution after protease reaction | 400 μl |
| 0.1 M Tris-HCl buffer (pH 8.0) | 410 μl |
| 3 mM 4-amino antipyrine | 30 μl |
| 3 mM TOOS | 30 μl |
| 60 U/ml POD | 30 μl |
| 0.5602 U/ml FAOD-S | 100 μl |

Figure 4:
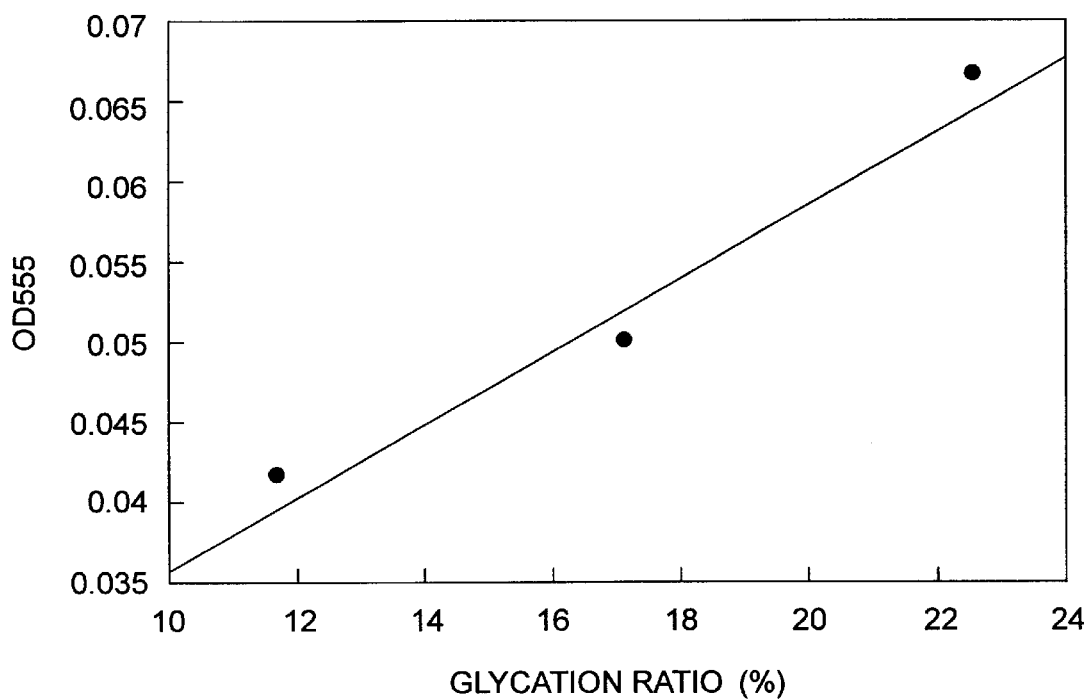
FIG. 4 is a graph showing the results of the measurement of glycation ratios of HSA by use of a commercially available protease (trade name: Sumizyme MP) in combination with FAOD-S (measurement of the glycation ratio with Sumizyme MP/FAOD-S) in Example.

As a result of the above-mentioned measurement, as shown in the graph of FIG. 4, when the above measuring system using "Sumizyme MP"/FAOD-S was used, it is confirmed that the glycation ratio of HSA was increased along with an increase in the quantity of color development. Further, there was obtained a positive correlation between the glycation ratio and the resultant absorbance, and therefore it was found that the method using this measurement system was useful for measuring the glycation ratio of HSA. (Measurement of glycation ratio of HSA using protease from A. melleus FERM BP-6277)

Then, with respect to the protease from A. melleus FERM BP-6277 which had been used for the above-mentioned GPC measurement of glycation ratio of HSA, experiments on the glycation ratio measurement for HSA were conducted in the same manner as in that using "Sumizyme MP." However, since it had been found that the protease activity was low, the reaction was conducted by adding 200 μl of the protease solution to 200 μl of 5 wt. % of HSA, and the reaction time was 5 hours.

Figure 5:
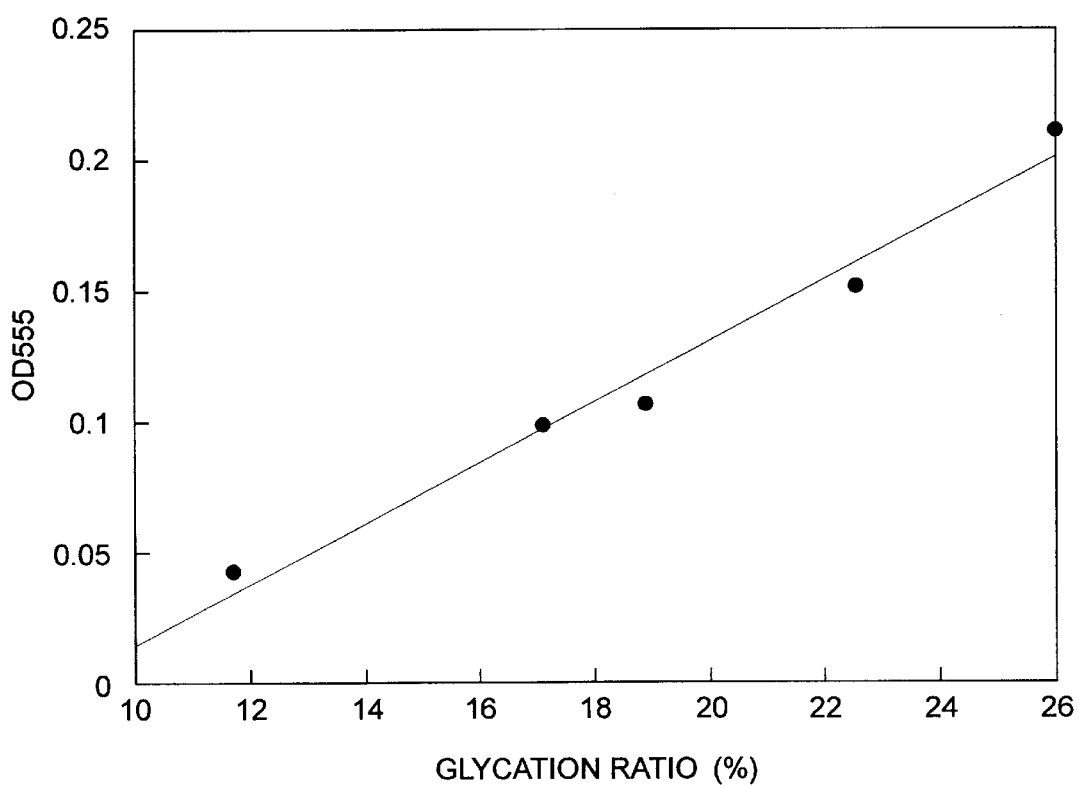
FIG. 5 is a graph showing the results of measurement of glycation ratios of HSA by use of the protease obtained in the example with the FAOD-S (measurement of the glycation ratios using *A. melleus* BP-6277/FAOD-S).

In the same manner as in the case using "Sumizyme MP", color development was confirmed by use of the FAOD-S. As a result, as shown in the graph of FIG. 5, a positive correlation was obtained as in the investigation using Sumizyme MP. Therefore, it was confirmed that the protease from A. melleus FERM BP-6277 was useful for the measurement of the glycation ratio of HSA similarly as in the case of "Sumizyme MP."

The graph in FIG. 5 does not cross with the origin. According to the present inventors' knowledge, it was presumed that an impurity in the protease and FAOD-S or a component of HSA were subjected to reaction and therefore they caused pseudo-color development. It was presumed that the graph approached the origin when the purity of the enzyme was improved.

Example 5

(Separation of protease having optimum pH in acidic range)

In this Example, A. melleus KDK 3001 (deposition number: FERM BP-6277) which was stored in Kyoto Daiichi Kagaku Co., Ltd., and four strains of A. melleus (A. melleus IFO 4339, A. melleus IFO 4220, A. melleus IFO 7541 and A. melleus IFO 32035) obtained from IFO (incorporated foundation: Research Institute for fermentation) were used as A. melleus.

Since the above-mentioned four strains obtained from IFO were stored in a freeze-dried state in ampoules, respectively, a renaturation solution was prepared in accordance with the designation of the supplier. Each of the four strains was renatured by use of 200 μl of the renaturation solution, and then was inoculated into a GPYM slant. After the thus obtained slant was cultured at 30° C. for 2 days, it was observed that all of the strains were grown. The composition of the GPYM slant used herein was as follows:

| | |
|---|---|
| Glucose | 1.0% |
| Pepton | 0.5% |
| Yeast extract | 0.3% |
| Malt extract | 0.3% |
| Agar | 2.0% |

(pH 5.5–6.0, sterilized by an autoclave, 120° C., for 20 minutes)

Each of the strains (five kinds of strains in total) was inoculated into 10 ml of a GPYM medium, and then was cultured at 30° C. for 2 days by a shaking culture method. Thereafter, the strain was transferred into 500 ml of the same medium, and then was further cultured for 2 days. The rate of shaking was 111 rpm for each of the cultures.

As a result of the above culture, all of the strains showed good growth. Then, bacterial cells were collected by filtration, and then the cells were weighed (wet weight). Since the protease as a target was expected to be an extracellular enzyme, the supernatant obtained by the above-mentioned procedure was used for the subsequent investigation. The composition of the GPYM slant used herein was as follows:

| | |
|---|---|
| Glucose | 1.0% |
| Pepton | 0.5% |
| Yeast extract | 0.3% |
| Malt extract | 0.3% |

(pH 5.5–6.0, sterilized by an autoclave, 120° C., for 20 minutes) 100 μl of the cultured supernatant after the collection of the bacterial cells was concentrated and partially purified by precipitation using ammonium sulfate. Since Sumizyme MP (commercially available) which was an enzyme (to be used in food industry) isolated and purified from A. melleus was stable in the vicinity of neutral pH value and the pH value of the cultured medium at the end of the culturing was approximately 4.6–5, the pH value was maintained at 6–6.5 during the ammonium sulfate precipitation.

In the ammonium sulfate precipitation, the ammonium sulfate was added under cooling in an ice bath, and after the addition of the ammonium sulfate, the mixture was stirred at 4° C. for an hour. After the completion of the stirring, the resultant mixture was centrifuged at 4° C. at 10000 rpm for 40 minutes so as to collect precipitate, and the resultant precipitate was dissolved in a minimum volume of distilled water and dialyzed against distilled water at 4° C. over night (semi-permeable membrane: dialysis membrane, mfd. by Sanko Jun-yaku Co., Ltd.). After the completion of the dialysis, the resultant internal fluid was centrifuged in a centrifugal micro-tube (4° C., 12,000 rpm, for 20 minutes). After the centrifugation, the resultant supernatant was collected.

The protease activity of each of the concentrated culture supernatants was measured. The above-mentioned "Sumizyme MP" was a weak-alkali protease having an optimum pH value in the neighborhood of 8. However, according to the present inventors' experiments, it was expected that a protease having an optimum pH value in the acidic range was present other than the weak-alkali protease, and therefore the measurement of the acid protease activity was confirmed.

As a substrate for the measurement of this protease activity, 5 wt. % of HSA (pH 5) was used. 20 μl of the concentrated culture supernatant obtained above, 20 μl of 5 wt. %-HSA and 60 μl of 0.1 M Tris-HCl buffer (pH 5) were mixed with each other, and the resultant mixture was then subjected to reaction at 37° C. for 30 minutes. Then, to the resultant mixture, 100 μl of 0.6 M trichloroacetic acid (TCA) was added, and the resultant mixture was left standing for 15 minutes or more under cooling in an ice bath, and then was subjected to centrifugation at 4° C. at 12000 rpm for 10 minutes (TCA precipitation). By use of 25 μl of the resultant supernatant from which protein had been removed by the TCA precipitation, the amount of free amino acids in the supernatant was measured by use of commercially available Bio-Rad DC Protein assay kit (mfd. by Bio-Rad Co.). The kit was used in a manner according to the supplier's instructions. At the time of the measurement of free amino acids, in order to avoid the effect of amino acids contained in the concentrated culture supernatant, a sample which had been obtained by mixing the above three kinds of solutions, and immediately thereafter subjecting the resultant mixture to the TCA precipitation was used as a blank (reference).

As a result, all of the five kinds of concentrated cultured supernatant corresponding to the above-mentioned five kinds of strains showed clear color development after the above reaction for 30 minutes, and therefore the presence of the protease activity was confirmed. Based on the confirmation of those protease activities, each of the partially purified concentrated cultured supernatants was used as a protease solution for the subsequent investigations.

Then, among the above-mentioned five kinds of strains, the solution containing the protease from *A. melleus* KDK 3001 strain was subjected to the measurement of the optimum pH value thereof.

In the measurement of the optimum pH value, first of all, 5 wt. % of HSA solutions having a pH value of 1.6 and a pH value of 8 were prepared as a substrate solution by use of 0.1 M Tris-HCl buffer, then by mixing these two solutions, ten kinds of substrate solutions having their pH values in the range of pH 1.6–pH 6.8 were prepared in total. Further, by adding hydrochloric acid to the HSA solution having a pH value of 1.6, a substrate solution having a pH value of 1 was prepared.

20 μl of each of the substrate solutions the pH values of which had been adjusted to each of the above-mentioned pH values, 20 μl of the protease-containing solution and 60 μl of distilled water were mixed with each other, and then the resultant mixture was subjected to reaction at 37° C. for 30 minutes. The pH value of the reaction mixture was measured again just before the reaction (i.e. just after the mixing of three solutions), and the pH value of the reaction mixture was measured again at the time of the protease reaction (just after mixing of the three solutions). As a result, it was found that the pH value of the reaction mixture was in the range of 1.6–6.5.

The enzyme activity was measured by removing protein by use of TCA precipitation and measuring the amount of free amino acids in the resultant supernatant by use of Bio-Rad DC Protein assay kit in the same manner as in the above-mentioned protease activity measurement.

Figure 6:
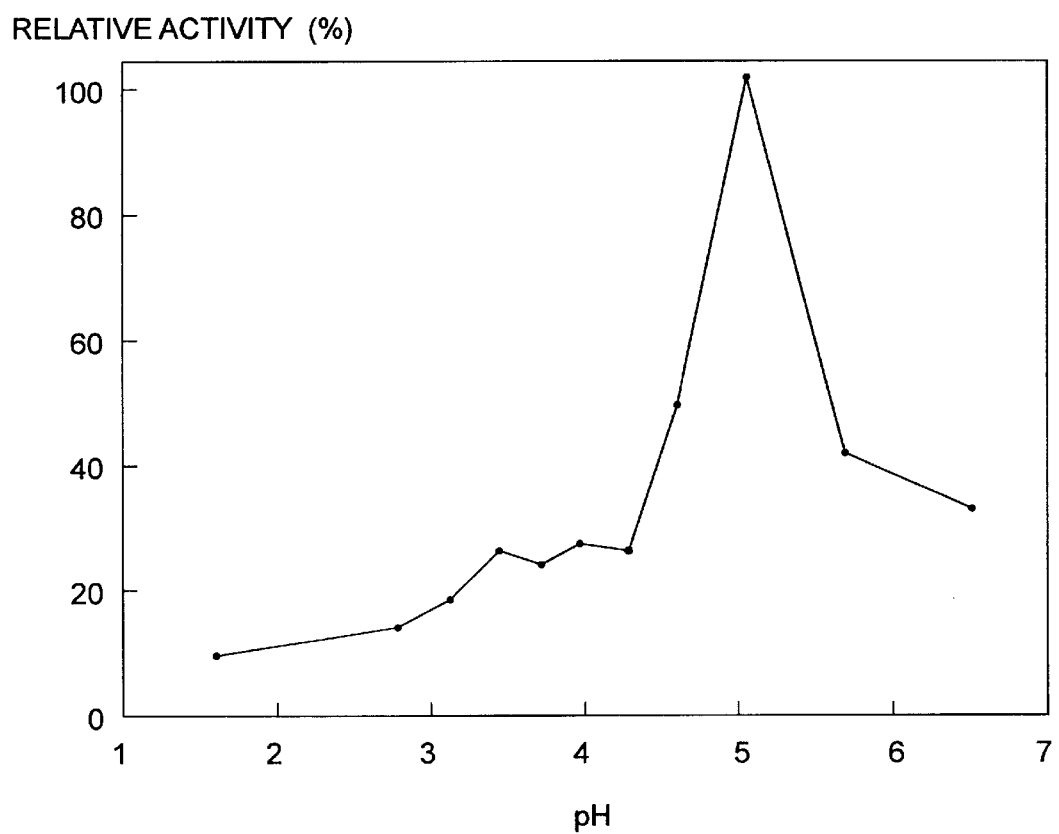
FIG. 6 is a graph showing the relative activity values of an acid protease obtained in Example at various pH values, provided that the activity value of the acid protease at pH 5 (optimum pH) is treated as "100" (reference).

As a result, it was confirmed that the acid protease from *A. melleus* KDK 3001, as shown in the graph of FIG. 6, was one having its optimum area in the range between pH 4.7 and pH 5.6 and having a particularly high activity at pH 5.

Figure 7:
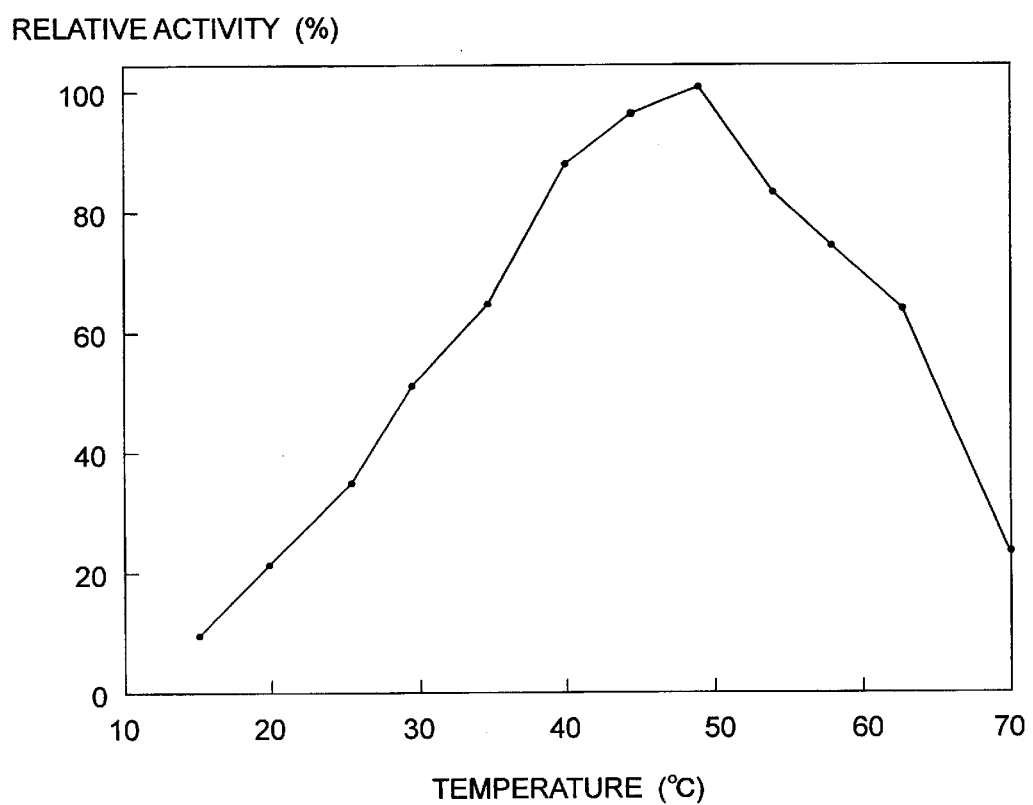
FIG. 7 is a graph showing the relative activity values of an acid protease obtained in Example at various temperatures, provided that the activity value of the acid protease at 50° C. (optimum temperature) is treated as "100".

The optimum temperature of the acid protease from *A. melleus* KDK 3001 was measured by fixing the pH value of the reaction mixture at pH 5 and changing the temperature from 15 to 70° C. at intervals of 5° C. After the incubation for 30 minutes, the protease activity was measured in the same manner as that described above. As a result, as shown in the graph of FIG. 7, the protease practically functioned in the range of 35–65° C., and had a high activity in the range of 40–50° C., and therefore it was found that the protease had its optimum temperature within this range. The protease showed the highest activity when the temperature was 50° C.

In order to roughly measure the molecular weight of the protease, the protease from *A. melleus* KDK 3001 was subject to GPC. Superdex 200 pg 16/60 (mfd. by Pharmacia Co.) was used as a column and fractions were collected at intervals of 30 seconds. In the GPC treatment, by measuring the protease activity of each of the collected fractions, the molecular weight of the protease was presumed by use of the time corresponding to the elution of the fraction. The measurement condition for the GPC used herein were as follows.

| <Measurement conditions of GPC> | |
|---|---|
| Column: | Superdex 200 pg 16/60 (mfd. by Pharmacia Co.) |
| Eluent: | 20 mM Tris-HCl buffer |
| Elution condition: | 0.5 ml/min |
| Temperature: | Room temperature |
| Detection: | UV detection (220 nm) |
| Volume of injected sample: | 50 μl |

In the measurement of the protease activity, in view of the dilution of protease during the GPC process, 80 μl of each fraction was added to 20 μl of 0.5 wt. % HSA, and the resultant mixture was subjected to reaction at 37° C. for 24 hours, and then the protease activity thereof was measured in the same manner as described above. The protease activity of each of the fractions obtained by the above-mentioned GPC was measured by the same measurement method as described above, and it was estimated that the molecular weight of the protease from this strain was 18382–22130.

Example 6

(Measurement of glycated protein by use of acid protease)

In this Example, based on the advantage that the protease obtained in Example 5 had its optimum pH value in the acidic range while the optimum pH value of the FAOD was 8, the protease activity was inactivated by adjusting the pH value to the optimum pH value of the FAOD (pH 8) after the protease treatment, without heating or adding an inhibitor.

By use of a solution containing the protease which had been isolated and purified from *A. melleus* KDK 3001, human serum albumin (HSA: Sigma Co., "ALUBUMIN HUMAN FRACTION V", and Bayer Co., "Albumin FrV") having different glycation ratios were subjected to the measurement. The glycation ratios of these HSAs were 11.7%, 22.5% and 26.0%, respectively. These glycation ratios were measured in advance by use of GAA-2000 (HPLC method) mfd. by Kyoto Daiichi Kagaku Co., Ltd.

In the subsequent measurement of the glycated HSA by using an enzymatic method, the above-mentioned various glycated HSAs were used after they were adjusted to a concentration of 5 wt. % and a pH value of 5. Further, by mixing HSA samples having different glycation ratios, samples having their glycation ratios of 17.1% and 18.85% were also prepared. By use of these five kinds of samples having different glycation ratios, the glycated HSA was measured by use of the protease-containing solution obtained in Example 5.

However, since it had been found that the protease activity obtained in Example 5 was low, 200 μl of the protease-containing solution of Example 5 was added to 200 μl of 5 wt. % of HSA so as to cause the reaction, and the reaction time was 5 hours. After the reaction using this protease, the resultant color development was confirmed by use of the FAOD (FAOD-S). As the FAOD, the FAOD-S which had been prepared according to JP-A Hei-7-289253 (0.5602 U/ml) was used.

The titer of the FAOD used in this Example was measured by the above-mentioned rate method. The composition of the reactant solution of the FAOD color-developing system used for the above-mentioned titer determination was as follows.

| | |
|---|---|
| Solution after the above protease reaction | 400 μl |
| 0.1 M Tris-HCl buffer (pH 8.0) | 410 μl |
| 3 mM 4-Aminoantipyrine | 30 μl |
| 3 mM TOOS | 30 μl |
| 60 U/ml POD (peroxidase) | 30 μl |
| 0.5602 U/ml the FAOD-S | 100 μl |

After the FAOD color-developing solution having the above-mentioned composition was incubated at 37° C. for 30 minutes, the absorbance thereof at 555 nm was measured. With respect to each of the above samples, a blank (i.e. the absorbance of the reference solution containing no substrate) was also measured, and the absorbance of the blank was subtracted from the absorbance of each sample obtained by the above step, thereby to obtain the actual absorbance.

Figure 8:
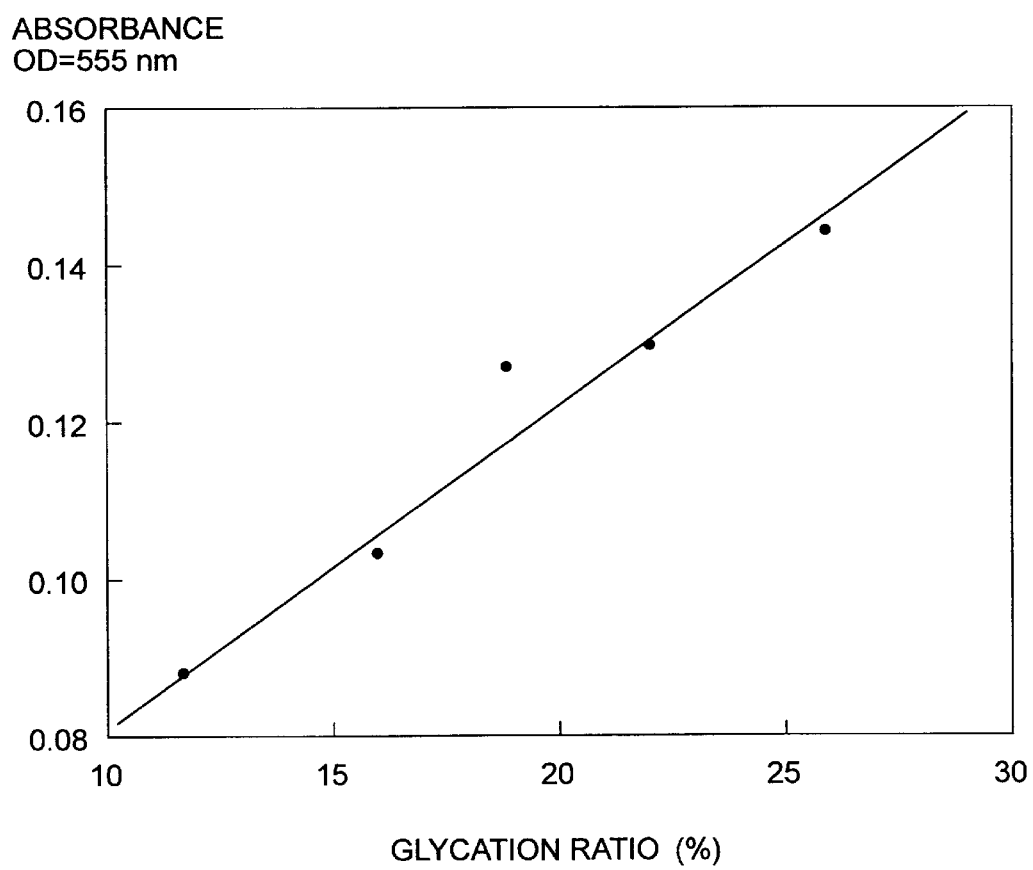
FIG. 8 is a graph showing the results of the absorbance measurement based on the FAOD reaction with respect to various glycation ratios of HSA (human serum albumin) in Example.

As a result of the above measurement, as shown in the graph of FIG. 8, the color-developing reaction was caused by the FAOD corresponding to the glycation ratio of the HSA. Accordingly, it was confirmed that the acid protease obtained by this Example was sufficiently usable for measuring a glycated protein in combination with the FAOD.

The graph in FIG. 8 does not cross with the origin. According to the present inventors' knowledge, it was presumed that the corresponding color development was attributable to an impurity in the protease and FAOD or a component of HSA used herein. It was presumed that the graph approached the origin when the purity of the enzyme was improved.

Industrial Applicability

As described hereinabove, according to the present invention, there is provided a protease to be used for measuring a glycated protein in a sample in combination with FAOD (fructosyl amino acid oxidase).

The present invention also provides a method of measuring a glycated protein by causing FAOD to act on a sample containing a glycated protein, wherein the glycated protein is treated with a protease under an acid condition.

The present invention further provides a method of measuring a glycated protein by causing protease and FAOD to act on a sample containing a glycated protein, wherein a protease from Aspergillus genus is used as the protease.

The present invention further provides a method of measuring a glycated protein by causing protease and FAOD to act on a sample containing a glycated protein, wherein Protease XIV is used as the protease.

In the above-mentioned method according to the present invention, a glycated protein in a living organism component can be measured with high sensitivity and accuracy by using a suitable protease which exhibits a useful enzymatic action in combination with an FAOD suitably usable for measuring glycated albumin. Accordingly, the present invention provides a method of measuring a glycated protein which can contribute to the control and prevention of symptom of diabetes, and also provides a protease which is suitably usable for such a method.

Further, according to an embodiment of the present invention using an easily available protease, such as "Sumizyme MP" as the above-mentioned protease, the present invention becomes applicable to clinical use more widely.

In addition, according to an embodiment of the present invention using an acid protease, the above-mentioned protease can be inactivated easily and rapidly by adjusting the pH value, and therefore the present invention is applicable to clinical examination, etc., more widely.

What is claimed is:

1. A protease to be used for measuring a glycated protein in a sample in combination with FAOD (fructosyl amino acid oxidase), which protease is obtained from the *Aspergillus* genus.

2. The protease according to claim 1, which is from *Aspergillus melleus*.

3. A method of measuring a glycated protein by causing FAOD to act on a sample containing a glycated protein, wherein the glycated protein is treated with a protease from the *Aspergillus* genus under an acid condition.

4. A method according to claim 3, wherein the FAOD is FAOD-S or FAOD-G.

5. A method according to claim 3, wherein the glycated protein is glycated albumin.

6. A method of measuring a glycated protein by causing protease and FAOD to act on a sample containing a glycated protein, wherein a protease from *Aspergillus melleus* (*A. melleus*) is used as the protease.

7. A method according to claim 6, wherein the protease was a protease from *A. melleus* and the protease has its optimum pH value in acid range.

8. A method according to claim 7, wherein the protease from *A. melleus* is Sumizyme MP.

9. A method according to claim 6, wherein the FAOD is FAOD-S or FAOD-G.

10. A method according to claim 6, wherein the glycated protein is glycated albumin.

11. A method of measuring a glycated protein by causing protease and FAOD to act on a sample containing a glycated protein, wherein Protease XIV is the protease.

12. A method according to claim 11, wherein the FAOD is FAOD-S or FAOD-G.

13. A method according to claim 11, wherein the glycated protein is glycated albumin.

14. The method according to claim 3, wherein the protease is from *Aspergillus melleus*.

15. A method of measuring a glycated protein by causing FAOD to act on a sample containing a glycated protein, wherein the glycated protein is treated with a protease from *Aspergillus* genus under an alkaline condition.

16. The method according to claim 15, wherein the protease is from *Aspergillus melleus*.

17. The method according to claim 15, wherein the glycated protein is glycated albumin.

18. The method according to claim 15 wherein the wherein the FAOD is FAOD-S or FAOD-G.

* * * * *